(12) United States Patent
Asada et al.

(10) Patent No.: US 8,267,854 B2
(45) Date of Patent: Sep. 18, 2012

(54) ENDOSCOPE SYSTEM

(75) Inventors: Daisuke Asada, Hachioji (JP); Keiji Handa, Hachioji (JP); Hitoshi Karasawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1140 days.

(21) Appl. No.: 12/133,006

(22) Filed: Jun. 4, 2008

(65) Prior Publication Data

US 2008/0312500 A1    Dec. 18, 2008

(30) Foreign Application Priority Data

Jun. 14, 2007    (JP) ................. 2007-157949

(51) Int. Cl.
*A61B 1/00*    (2006.01)
*A61B 1/04*    (2006.01)
*A61B 1/06*    (2006.01)

(52) U.S. Cl. .................. 600/114; 600/160

(58) Field of Classification Search .......... 600/104, 600/114, 109, 160
See application file for complete search history.

(56) References Cited

U.S. PATENT DOCUMENTS

| | | | |
|---|---|---|---|
| 6,986,738 B2 * | 1/2006 | Glukhovsky et al. | 600/109 |
| 7,169,104 B2 * | 1/2007 | Ueda et al. | 600/104 |
| 2002/0103417 A1 * | 8/2002 | Gazdzinski | 600/109 |
| 2005/0085697 A1 * | 4/2005 | Yokoi et al. | 600/160 |
| 2005/0165272 A1 * | 7/2005 | Okada et al. | 600/114 |
| 2006/0074307 A1 * | 4/2006 | Igarashi et al. | 600/434 |
| 2007/0161855 A1 * | 7/2007 | Mikkaichi et al. | 600/113 |
| 2007/0255100 A1 * | 11/2007 | Barlow et al. | 600/114 |
| 2008/0015413 A1 * | 1/2008 | Barlow et al. | 600/114 |

FOREIGN PATENT DOCUMENTS

| | | |
|---|---|---|
| JP | 7-194602 | 8/1995 |
| JP | 07-323002 | 12/1995 |
| JP | 2005-230450 | 9/2005 |
| JP | 2005-323681 | 11/2005 |
| JP | 2007-117188 | 5/2007 |
| WO | 2007/061386 | 5/2007 |

OTHER PUBLICATIONS

Chinese Office Action dated Jan. 8, 2010.

* cited by examiner

*Primary Examiner* — Philip R Smith
(74) *Attorney, Agent, or Firm* — Scully, Scott, Murphy & Presser, P.C.

(57) ABSTRACT

An endoscope system includes a camera for picking up an image inside a body cavity, a camera side magnet connected to the camera and a fixing magnet, for fixing the camera inside the body cavity by holding an abdominal wall from different surfaces of the abdominal wall, and a second CCU for controlling the camera.

2 Claims, 11 Drawing Sheets

ENDOSCOPE SYSTEM

CROSS REFERENCE TO RELATED APPLICATION

This application claims benefit of Japanese Patent Application No. 2007-157949 filed on Jun. 14, 2007, the contents of which are incorporated by this reference.

BACKGROUND OF THE INVENTION

1. Field of the Invention

The present invention relates to an endoscope system including an image pickup apparatus capable of viewing an interior of an abdominal cavity in a wide range and fixed to an interior side of an abdominal cavity wall.

2. Description of the Related Art

In recent years, there have been performed laparoscopic surgeries in which a trocar for guiding an endoscope for observation into a body cavity and a trocar for guiding a treatment instrument to an area to be treated are inserted into a patient abdomen and curative treatment is performed by observing the treatment instrument and the area to be treated by the endoscope without laparotomy for the purpose of reducing invasion to patients.

For example, in FIGS. 1 to 4 of Japanese Patent Laid-Open No. 07-323002, there is disclosed a trocar in which an operation knob is operated with a side portion of a distal end configuration portion being pressed to an abdominal wall, to fix the distal end configuration portion to the abdominal wall and open a distal end side by separating the distal end configuration portion from its body. The distal end configuration portion fixed to the abdominal wall is equipped with an image pickup apparatus for picking up images inside an abdominal cavity.

Also, for example, in FIG. 2 of Japanese Patent Laid-Open No. 2005-323681, there is disclosed a body cavity observation apparatus in which an observation unit is disposed in the vicinity of a puncture position of a trocar. The observation unit is fixedly put in an incision opened by cutting an abdomen.

SUMMARY OF THE INVENTION

An endoscope system includes: an image pickup section for picking up an image inside a body cavity; a fixing section connected to the image pickup section and fixing the image pickup section inside the body cavity by holding a body wall from different surfaces of the body wall; and a control section for controlling the image pickup section.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below with reference to the drawings.

Figure 1:
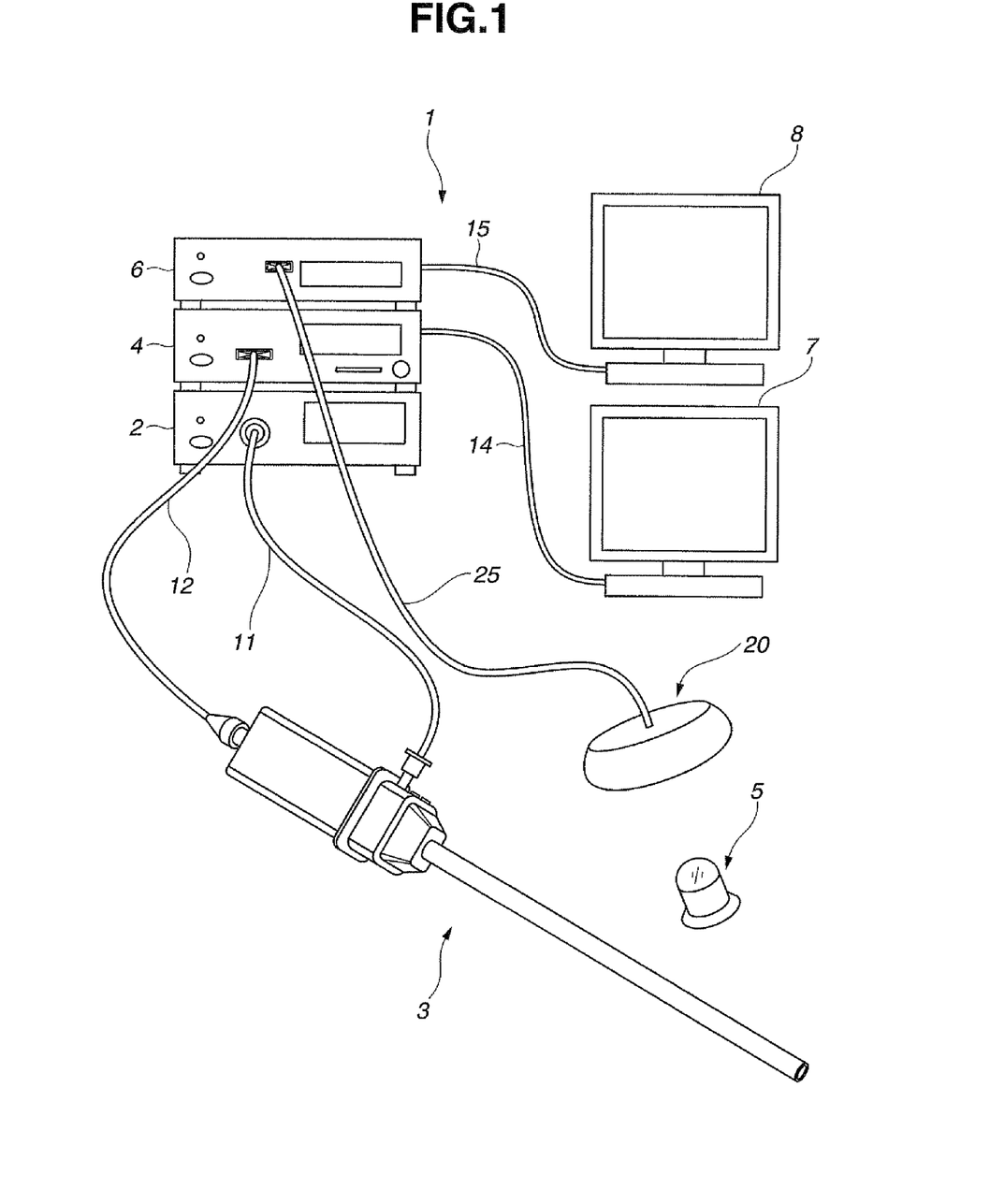
FIG. 1 is a view for explaining an endoscope system according to one embodiment.
Figure 2:
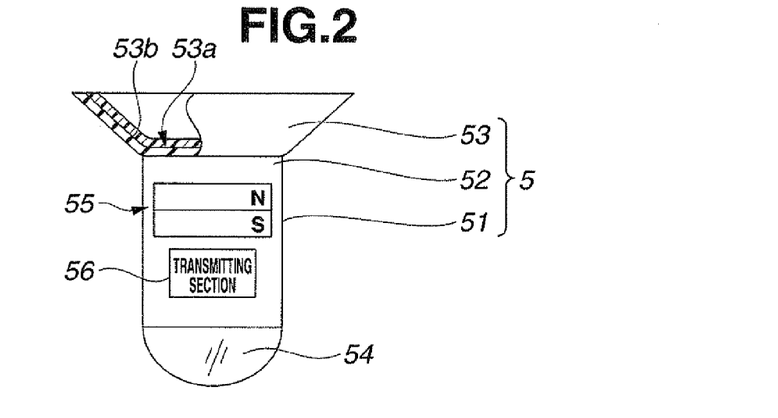
FIG. 2 is a schematic view for explaining a configuration of a camera placed on a body cavity wall (abdominal wall)
Figure 3:
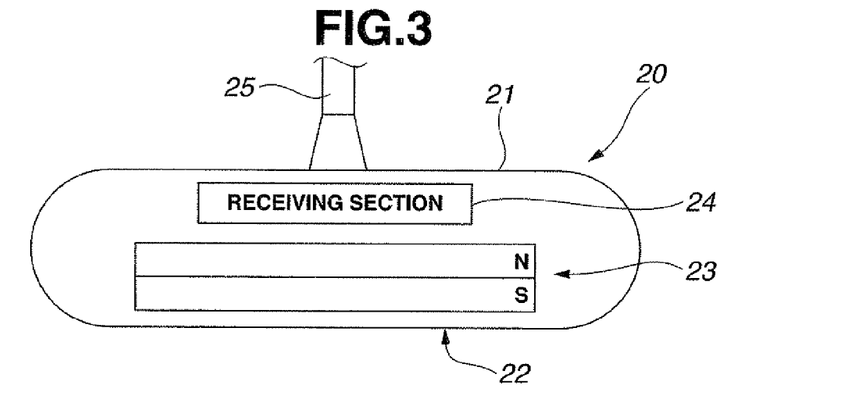
FIG. 3 is a schematic view for explaining a configuration of a camera fixing device.
Figure 4:
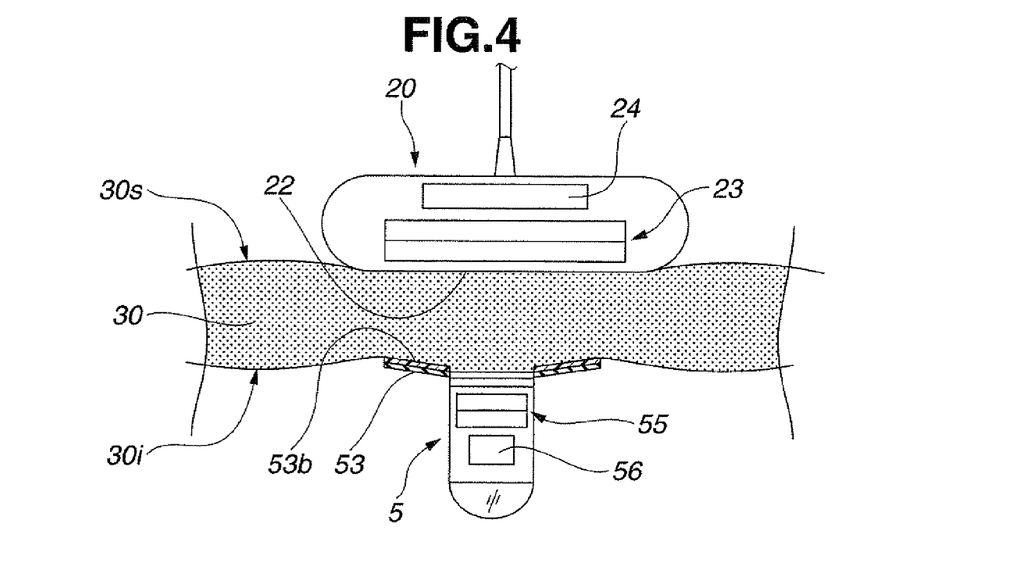
FIG. 4 is a view for explaining a state in which a camera is disposed by holding a body cavity wall (abdominal wall) by an attractive force between a fixing magnet and a camera side magnet.
Figure 5:
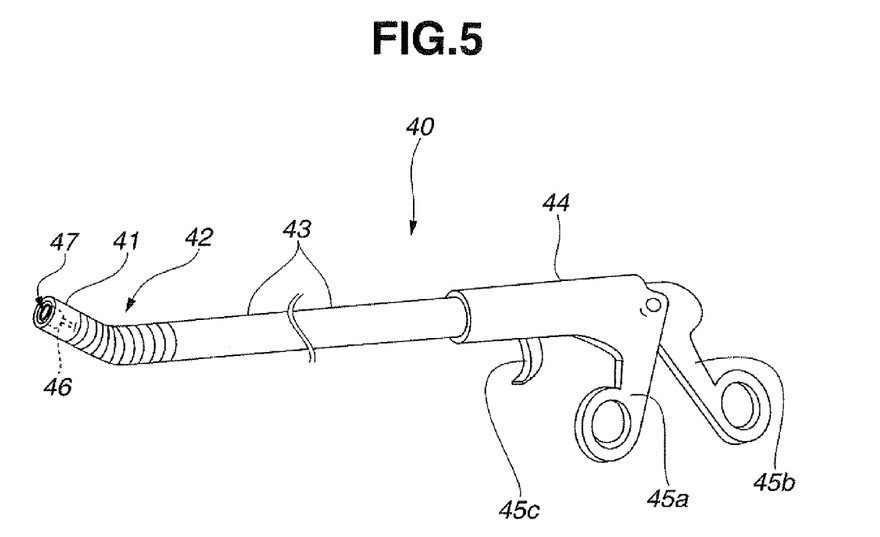
FIG. 5 is a view for explaining a configuration example of a camera attaching and removing forceps.
Figure 6:
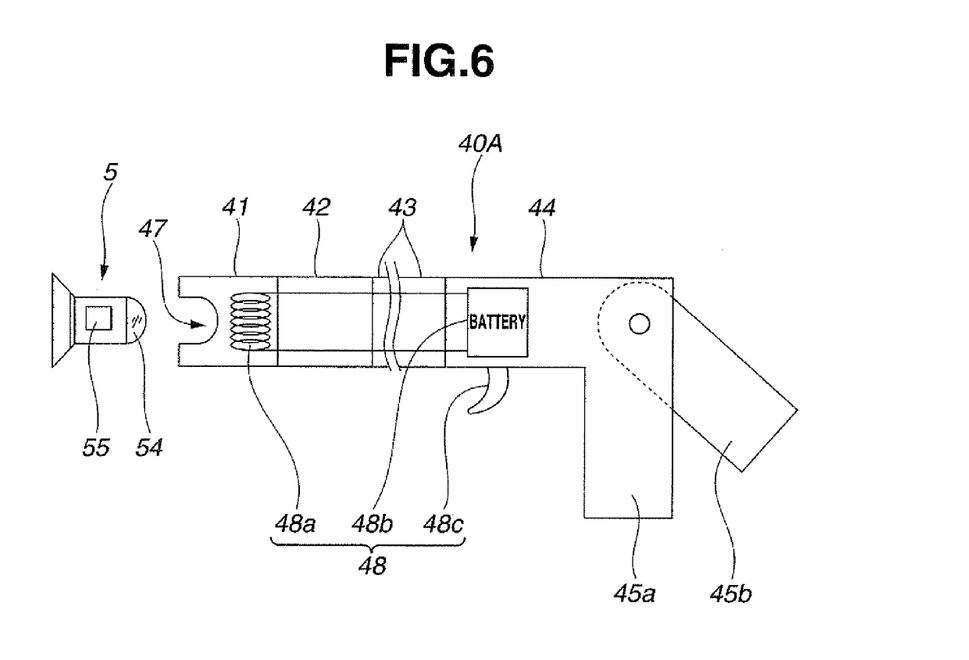
FIG. 6 is a view for explaining another configuration example of the camera attaching and removing forceps.
Figure 7:
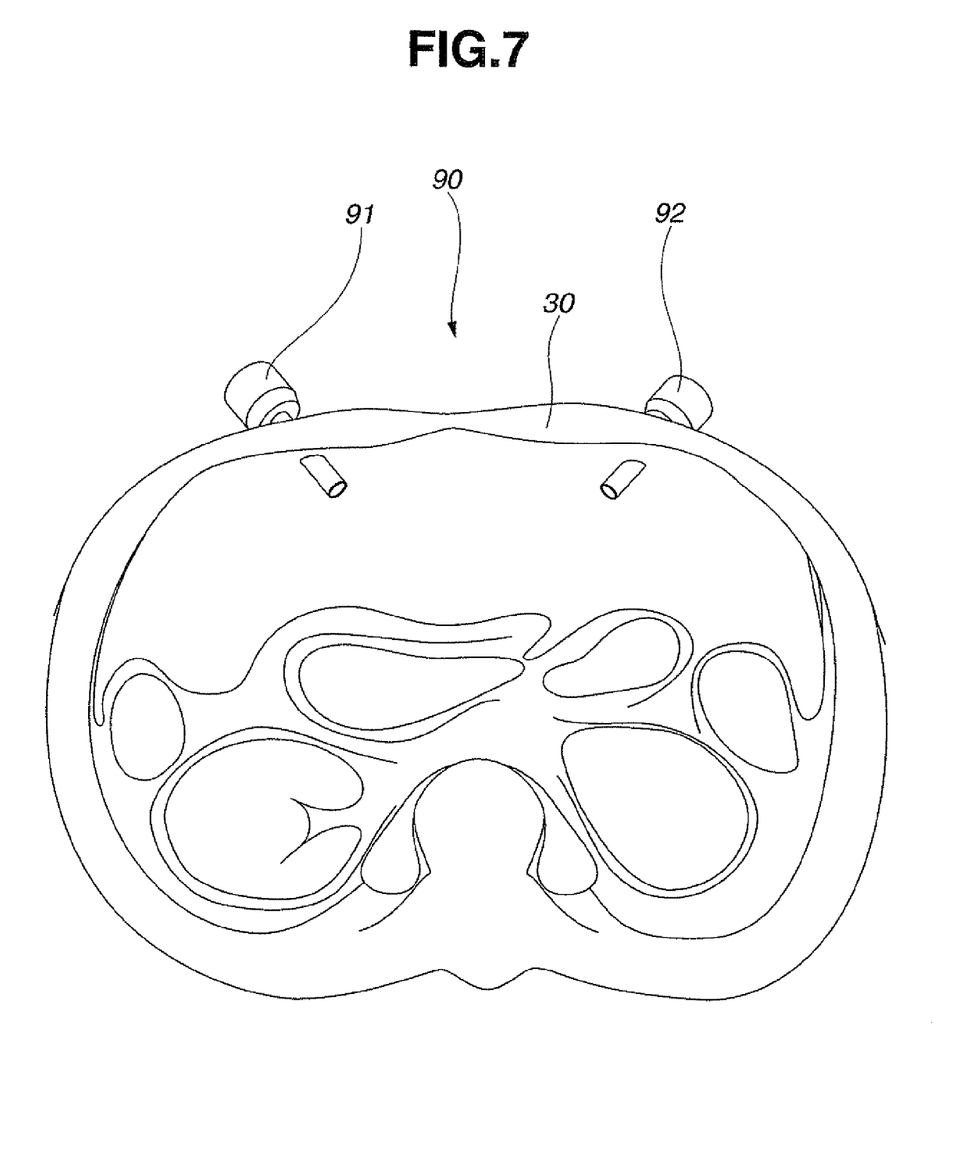
FIG. 7 explains an abdominal wall through which trocars are penetrated.
Figure 8:
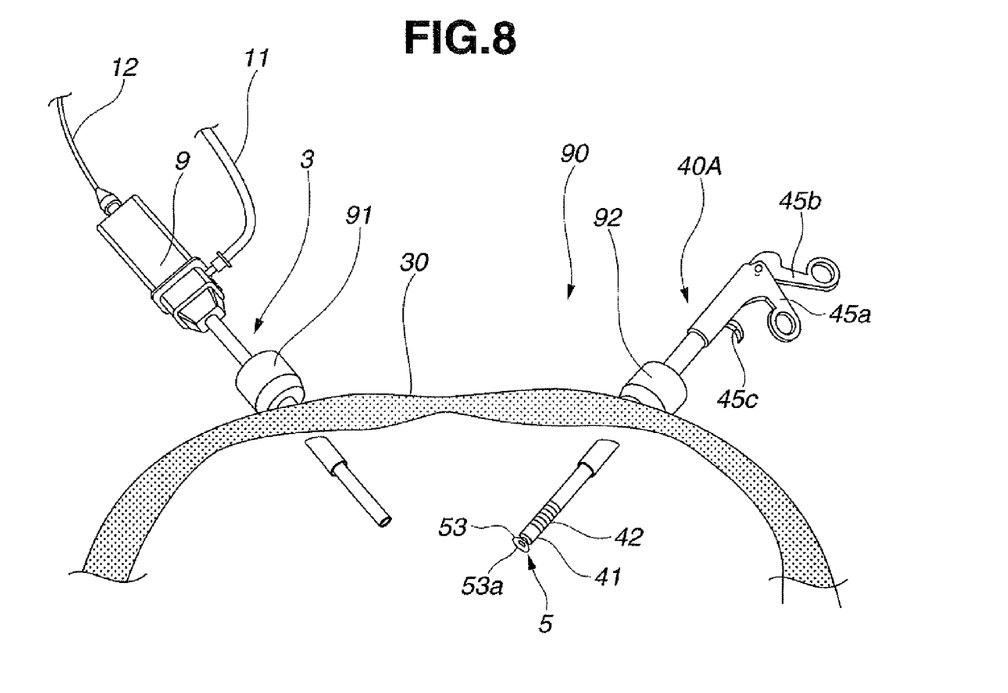
FIG. 8 is a view for explaining a state in which a rigid endoscope is inserted into one trocar and a camera attaching and removing forceps in which a camera body is disposed in a camera receiving portion is inserted into the other trocar in order to dispose the camera on an abdominal wall.
Figure 9:
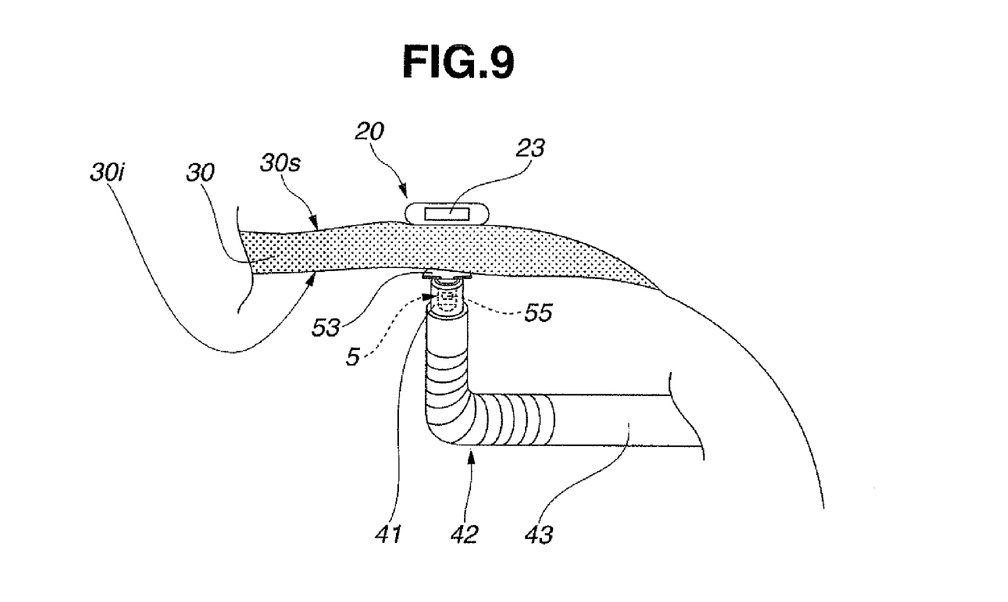
FIG. 9 is a view for explaining a state in which an elastic contact surface portion of a camera is brought into contact with an inner surface of an abdominal wall by operating a camera attaching and removing forceps.
Figure 10:
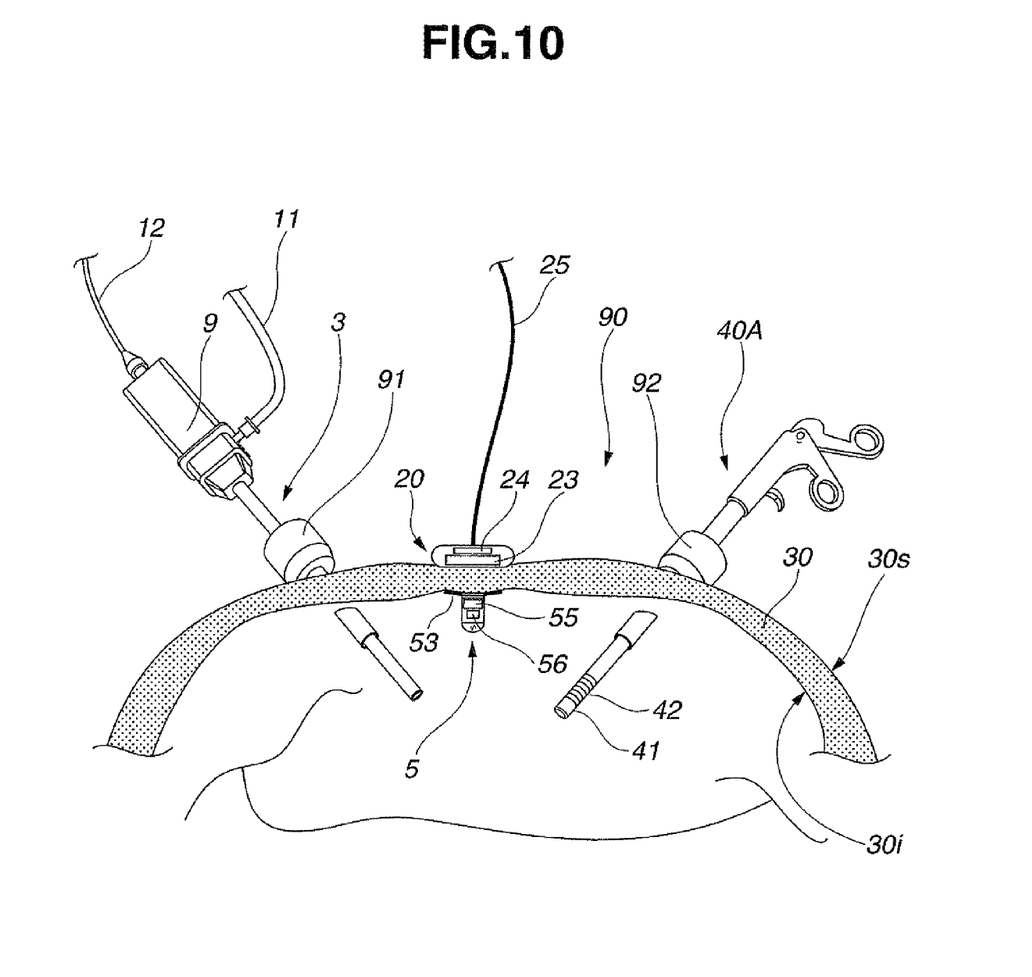
FIG. 10 is a view for explaining a state in which a camera is disposed on an inner surface of an abdominal wall.
Figure 11:
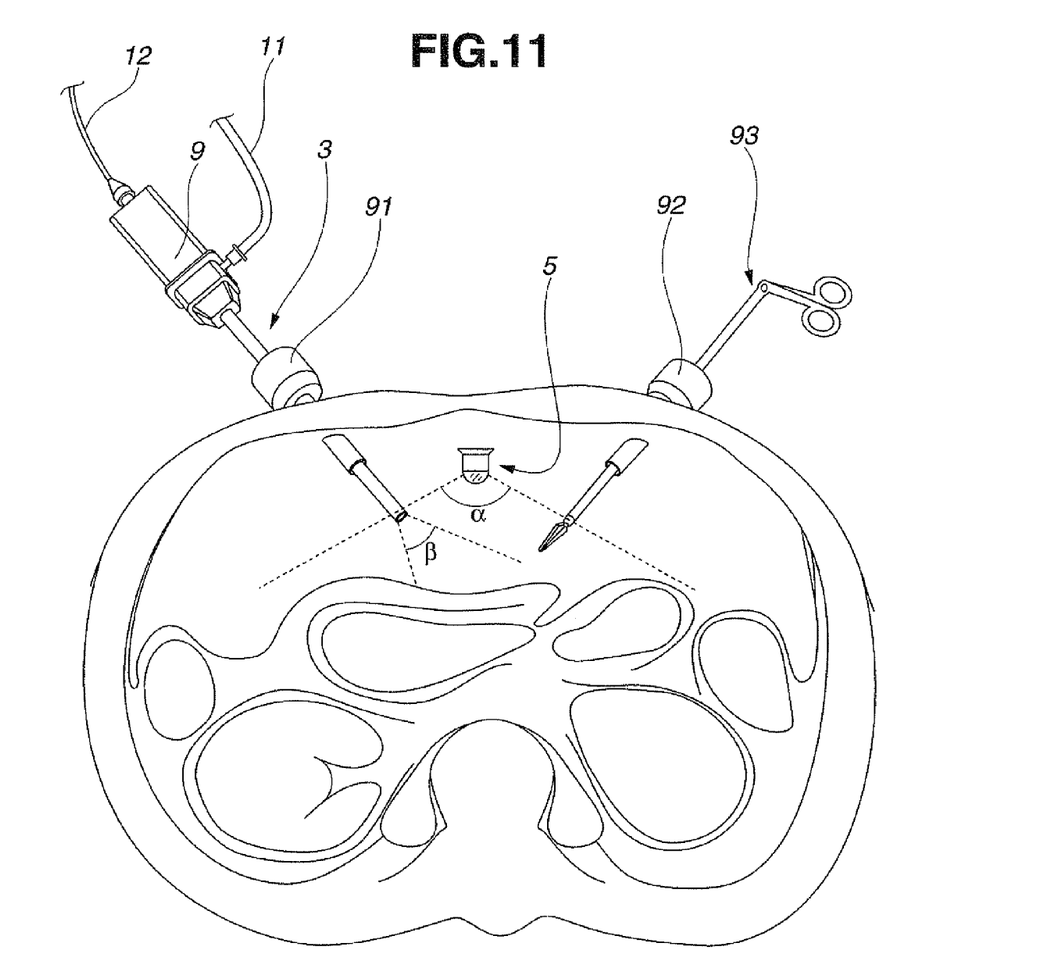
FIG. 11 is a view for explaining a state in which a surgical operation is performed by inserting a rigid endoscope into one trocar and inserting a grasping forceps into the other trocar.
Figure 12:
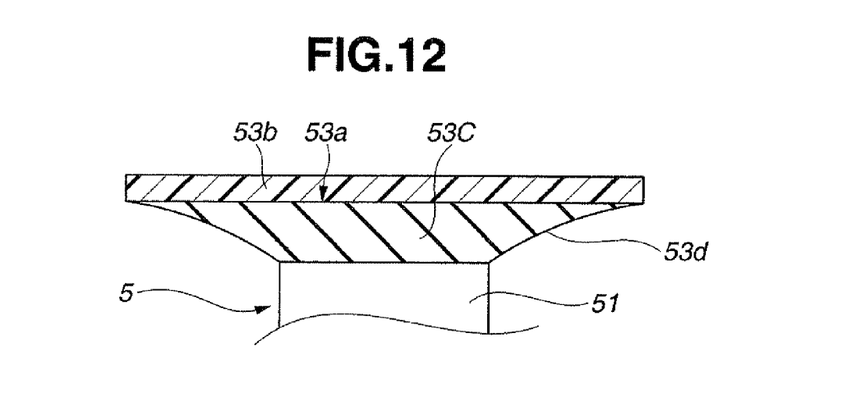
FIG. 12 is a view for explaining another configuration example of the elastic contact surface portion.
Figure 13:
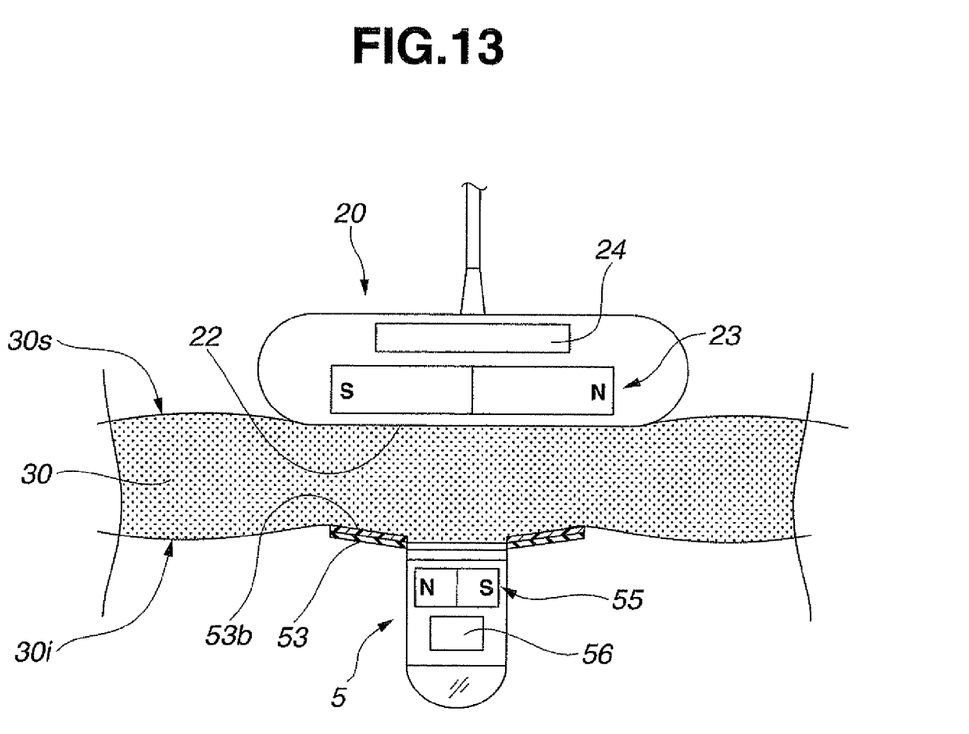
FIG. 13 is a view for explaining a state in which a camera is disposed by holding a body cavity wall (abdominal wall) by an attractive force between a fixing magnet in which a north pole and a south pole are disposed in parallel with an outer surface and a camera side magnet in which a north pole and a south pole are disposed in parallel with an inner surface.

FIGS. 1 to 13 are related to one embodiment of an endoscope system. FIG. 1 is a view for explaining an endoscope system; FIG. 2 is a schematic view for explaining a configuration of a camera placed on a body cavity wall (abdominal wall); FIG. 3 is a schematic view for explaining a configuration of a camera fixing device; FIG. 4 is a view for explaining a state in which a camera is disposed by holding a body cavity wall (abdominal wall) by an attractive force between a fixing magnet and a camera side magnet; FIG. 5 is a view for explaining a configuration example of a camera attaching and removing forceps; FIG. 6 is a view for explaining another configuration example of the camera attaching and removing forceps; FIG. 7 is a view for explaining an abdominal wall through which trocars are penetrated; FIG. 8 is a view for explaining a state in which a rigid endoscope is inserted into one trocar and a camera attaching and removing forceps in which a camera body is disposed in a camera receiving portion is inserted into the other trocar in order to dispose the camera on an abdominal wall; FIG. 9 is a view for explaining a state in which an elastic contact surface portion of a camera is brought into contact with an inner surface of an abdominal wall by operating a camera attaching and removing forceps; FIG. 10 is a view for explaining a state in which a camera is disposed on an inner surface of an abdominal wall; FIG. 11 is a view for explaining a state in which a surgical operation is performed by inserting a rigid endoscope into one trocar and inserting a grasping forceps into the other trocar; FIG. 12 is a view for explaining another configuration example of the elastic contact surface portion; and FIG. 13 is a view for explaining a state in which a camera is disposed by holding a body cavity wall by an attractive force between a fixing magnet in which a north pole and a south pole are disposed in parallel with an outer surface and a camera side magnet in which a north pole and a south pole are disposed in parallel with an inner surface.

As shown in FIG. 1, an endoscope system 1 according to the present embodiment for performing a surgical operation mainly includes a light source 2, a rigid endoscope 3, a first camera control unit (abbreviated to CCU below) 4, a camera 5 placed in a body cavity wall (abdominal wall 30) (abbreviated to camera below), which is image pickup means, a second CCU 6, a first display device 7, a second display device 8, and a camera fixing device 20 which doubles as a receiving device.

The light source 2 supplies an illumination light to an illumination optical system of the rigid endoscope 3. The light source 2 and the rigid endoscope 3 are removably connected to each other by a light source cable 11. The rigid endoscope 3 has an eyepiece in its proximal end portion, to which a rigid endoscope camera 9 is attached.

An optical image of an observed area illuminated by the illumination light supplied from the light source 2 to the rigid endoscope 3 is picked up by the rigid endoscope camera 9 attached to the eyepiece. The rigid endoscope camera 9 photoelectrically converts the picked-up optical image to an image pickup signal, and transmits the image pickup signal via an image pickup cable 12 to the first CCU 4.

The first CCU 4 produces a video signal from the transmitted image signal and outputs the video signal to the first display device 7. The first display device 7 is, for example, a liquid crystal display, and receives the video signal outputted from the first CCU 4 to display an endoscope image of the observed area on a screen.

As shown in FIGS. 1 and 2, the camera 5 includes a camera body 51, a base portion 52, and an elastic contact surface portion (abbreviated to elastic portion below) 53. A hemispherically-shaped transparent hood 54 is provided to the camera body 51. A camera side magnet 55 which is a first magnet, a wireless transmitting section 56, and an image pickup section, an illuminating section, a control section, a power section, or the like, which are not shown, are disposed in the camera body 51.

The image pickup section incorporated in the camera body 51 is an image pickup device such as CCD and C-MOS and the like. The incorporated illuminating section is a light emitting device such as LED. A predetermined wide-angle lens is disposed on a front surface of the image pickup section and the illuminating section. The image pickup section widely picks up an optical image inside a wide range of a body cavity illuminated by an illumination light. An image signal outputted from the image pickup section is transmitted via the wireless transmitting section 56 to a receiving section of the camera fixing device 20 described below.

The base portion 52 is a columnar member formed with an elastic member. The elastic portion 53 is fixed to a distal end surface of the base portion 52.

The elastic portion 53 is configured to be suction disk shape, a central portion of which is depressed, by a rubber member or a resin member having flexibility, and includes a contact surface 53a which deforms along an irregular body surface. The central portion of the elastic portion 53 is fixed to the distal end surface of the base portion 52.

An adhesive layer 53b is provided over an entire surface of the contact surface 53a. An adhesive which constitutes the adhesive layer 53b is a reinforcement material for fixing the camera 5 to a surface of a body cavity wall (abdominal wall 30). The adhesive is a water activated adhesive. For example, the adhesive exerts an adhesive force when a predetermined period of time passes after the adhesive is brought into contact with a body fluid of an abdominal wall, or a body fluid of an intestinal wall.

The camera side magnet 55 constitutes a fixing section which is fixing means. For example, a north pole is disposed facing the elastic portion 53 and a south pole is disposed facing the transparent hood 54.

As shown in FIGS. 1 and 3, the camera fixing device 20 includes, for example, an approximately cylindrical-shaped device body 21. The device body 21 includes a fixation surface 22 constituted by a plane surface to be disposed on a skin such as an abdomen of a patient. The device body 21 is configured with a curved surface in order to prevent damage to a patient or the like.

At least a fixing magnet 23 constituting the fixing section which is fixing means, and a receiving section 24 are incorporated in the device body 21. A signal cable 25 is extended from, for example, a top surface in the drawing opposite to the fixation surface 22 of the camera fixing device 20. An end portion of the signal cable 25 is connected to the second CCU 6 via a connector.

The fixing magnet 23 is a second magnet, and for example, a north pole is disposed facing an extension direction of the signal cable and a south pole is disposed facing the fixation surface 22. The receiving section 24 receives a signal transmitted from the wireless transmitting section 56 of the camera 5, and transmits the image signal outputted from the image pickup section of the camera 5 via an image signal line in the signal cable 25 to the second CCU 6.

The second CCU 6 constitutes a control section which is control means of the camera 5, and produces a video signal from the transmitted image signal to output the video signal to the second display device 8. The second display device 8 is also a liquid crystal display, and receives the video signal outputted from the second CCU 6 to display a camera image on a screen.

In FIG. 1, reference numeral 14 denotes a first video cable, and reference numeral 15 denotes a second video cable. The first video cable 14 connects the first CCU 4 and the first display device 7, and the second video cable 15 connects the second CCU 6 and the second display device 8.

Since the second video cable 15 is connected to the second display device 8, the video signal transmitted from the first CCU 4, and the video signal transmitted from the second CCU 6 can be displayed on the screen of the second display device 8 at the same time or alternately.

As shown in FIG. 4, the camera 5 is fixed (disposed) to an inner surface 30i of the abdominal wall 30, for example, with the fixation surface 22 of the camera fixing device 20 being disposed on an outer surface 30s of the abdominal wall 30. In the fixed state, the contact surface 53a of the elastic portion 53 deforms elastically and spreads, and an approximately entire surface of the contact surface 53a contacts the inner surface 30i. At this time, the camera 5 is fixed to the inner surface 30i by an attractive force between a magnetic force of the fixing magnet 23 of the camera fixing device 20 and a magnetic force of the camera side magnet 55 of the camera 5, and the adhesive force of the adhesive layer 53b provided to the contact surface 53a of the elastic portion 53.

In the present embodiment, the adhesive which constitutes the adhesive layer 53b does not have an adhesive force enough to stably fix the camera 5 to a body cavity wall (abdominal wall 30). In other words, the camera 5 is not fixed to a body cavity wall (abdominal wall 30) only by the adhesive force of the adhesive layer 53b. Along with the adhesive force of the adhesive which constitutes the adhesive layer 53b, the camera 5 fixedly holds the abdominal wall 30 by the attractive force between the fixing magnet 23 disposed on the outer surface 30s of the abdominal wall 30 and the camera side magnet 55 disposed on the inner surface 30i of the abdominal wall 30.

The camera 5 is disposed on the inner surface 30i of the abdominal wall 30, for example, by using a camera attaching and removing forceps (abbreviated to attaching and removing forceps below) 40 as shown in FIG. 5.

The attaching and removing forceps 40 shown in FIG. 5 includes a distal end portion 4l, a bending portion 42, a shaft portion 43, and an operation portion 44, which are successively disposed from a distal end side. The operation portion 44 includes a pair of bending handles 45a and 45b for performing a bending operation of the bending portion 42, and a puncture lever 45c.

The bending handle 45a is a fixed handle disposed so as to be integrated with the operation portion 44. The bending handle 45b is a rotation handle pivotally supported at the operation portion 44. The puncture lever 45c is a rotatable lever with respect to the operation portion 44 and is operated when the camera 5 is pressed to a body wall. By operating the puncture lever 45c, a pushing head 46 denoted by a dashed line is moved toward the distal end side.

The shaft portion 43 is a rigid tubular member such as a stainless-steel tubular member. The bending portion 42 is configured so as to be bended in up and down directions in the drawing. A camera receiving portion 47 which is a concave portion in which the pushing head 46 is disposed is provided in the distal end portion 41. The transparent hood 54 which constitutes the camera 5 is to be disposed in the pushing head 46.

Note that a configuration of the attaching and removing forceps 40 is not limited to a configuration in which the pushing head 46 is provided, and an attaching and removing forceps 40A shown in FIG. 6 may be used. The attaching and removing forceps 40A includes an electromagnet 48. The electromagnet 48 includes a coil 48a disposed in a distal end portion 41, a battery 48b for supplying power to the coil 48a, and a switch 48c for switching supply and stop of power to the coil 48a.

In the attaching and removing forceps 40A, when the switch 48c is turned ON with the camera 5 being disposed in the camera receiving portion 47, power is supplied to the coil 48a. The camera side magnet 55 of the camera 5 is drawn and the camera 5 is retained in the camera receiving portion 47. In order to terminate the retention, the switch 48c is turned OFF.

A procedure for disposing the camera 5 on the inner surface 30i of the abdominal wall 30 will be described with reference to FIGS. 7 to 11.

First, an operator prepares the camera 5, the camera fixing device 20, and the attaching and removing forceps 40A in order to dispose the camera 5 on the inner surface 30i of the abdominal wall 30. The camera 5 is retained in advance in the camera receiving portion 47 of the attaching and removing forceps 40A by the operator.

As shown in FIG. 7, for example, two trocars 91 and 92 having insertion holes for guiding the rigid endoscope 3 and an operation instrument into an abdominal cavity are penetrated through predetermined positions of an abdomen of a patient 90. The rigid endoscope 3 is inserted into the trocar 91. An operation apparatus such as a grasping forceps, or the attaching and removing forceps 40A is inserted into the trocar 92. For example, one end portion of an insufflation tube, which is not shown, is attached to the trocar 91 and, for example, carbon dioxide gas or the like is injected as an insufflation gas into the abdominal cavity for the purpose of ensuring a visual field of the rigid endoscope 3 and ensuring a region in which the operation apparatus or the like is operated.

As shown in FIG. 8, the operator inserts the rigid endoscope 3 into the trocar 91 and inserts the attaching and removing forceps 40A, in which the camera 5 is retained in the camera receiving portion 47 at the distal end portion 41, into the trocar 92.

While checking the endoscope image displayed on the screen of the first display device 7, the operator operates the bending handle 45b of the attaching and removing forceps 40A, to bend the bending portion 42, for example, as shown in FIG. 9 and make the elastic portion 53 of the camera 5 approximately face the camera fixing device 20 across the abdominal wall 30.

The operator operates at hand the operation portion 44 of the attaching and removing forceps 40A, to bring the elastic portion 53 of the camera 5 into closer proximity to the inner surface 30i of the abdominal wall 30 and press the elastic portion 53 to the inner surface 30i.

Accordingly, the elastic portion 53 spreads and the contact surface 53a contacts the inner surface 30i. The adhesive force of the adhesive layer 53b of the contact surface 53a is thereby gradually exerted. Then, the operator adjusts a position of the camera fixing device 20 to an optimum position and turns OFF the switch 48c.

An attractive force of the electromagnet 48 disappears, and there is generated the attractive force between the magnetic force of the fixing magnet 23 of the camera fixing device 20 and the magnetic force of the camera side magnet 55 of the camera 5. Accordingly, the camera 5 is fixed by holding the abdominal wall 30 as shown in FIG. 10 by the above attractive force and the adhesive force of the adhesive layer 53b of the elastic portion 53.

That is to say, the camera 5 is fixed to the inner surface 30i of the abdominal wall 30 without dissection of the abdominal wall 30 and without providing a through hole which communicates the outer surface 30s and the inner surface 30i of the abdominal wall 30.

After confirming that the camera 5 has been fixed to the inner surface 30i of the abdominal wall 30 by the endoscope image displayed on the screen of the first display device 7, the operator operates the second CCU 6 to bring the camera 5 into an ON state. The camera image picked up by the camera 5 is displayed on the screen of the second display device 8. The operator removes the attaching and removing forceps 40A from the trocar 92, and inserts, for example, a grasping forceps 93 into the trocar 92 as shown in FIG. 11 to perform a surgical operation.

At this time, the operator performs the surgical operation while checking the endoscope image in an image pickup range β of the rigid endoscope 3 displayed on the screen of the first display device 7 and the camera image in an image pickup range a of the camera 5 displayed on the screen of the second display device 8.

After the surgical operation, the operator detaches the camera fixing device 20 from the patient abdomen. The attractive force between the magnetic force of the fixing magnet 23 of the camera fixing device 20 and the magnetic force of the camera side magnet 55 of the camera 5 thereby disappears and the camera 5 falls inside the abdominal cavity. The operator observes the endoscope image displayed on the screen of the first display device 7, and operates the grasping forceps 93 or the attaching and removing forceps 40A to retrieve the fallen camera 5 inside the abdominal cavity and remove the camera 5 from the body cavity.

As described above, by providing the camera side magnet to the camera to be disposed on the inner surface of the body cavity wall (abdominal wall 30), and providing the fixing magnet to the camera fixing device to be disposed on the outer surface of the body cavity wall (abdominal wall 30), the camera, by which an image with a wider visual field than the endoscope image can be obtained, is disposed by holding the body cavity wall (abdominal wall 30) without affecting low invasiveness. Accordingly, the operator can perform a surgical operation by visually checking both the endoscope image of the rigid endoscope inserted via the trocar into the body cavity and the camera image.

Since the camera includes the suction disk shape elastic portion and the adhesive layer is provided to the contact surface of the elastic portion as the reinforcement material, the camera is stably fixed to the body cavity wall (abdominal wall 30) by the attractive force between the magnets and the adhesive force of the adhesive layer without increasing the magnetic forces of the magnets.

Note that the elastic portion 53 is not limited to the suction disk shape, and such a configuration may be used that the elastic portion becomes gradually flexible from the central side toward the periphery as an elastic portion 53C shown in FIG. 12. The elastic portion 53C is configured such that, for example, a contact surface 53a is configured to be a plane and a shape changing portion 53d, thickness of which becomes gradually thinner from the center toward the periphery, is provided as shown in FIG. 12.

Accordingly, the elastic portion 53C can tightly adhere to a surface of a body wall which is concave and convex and is not flat. When a state of the body wall surface is changed depending on a patient posture or the like during a surgical operation, the elastic portion 53C easily follows the change to retain the tight adhesive state. The elastic portion 53C is directly and integrally fixed to a plane surface of the camera body 51.

As shown in FIG. 13, the north and south poles of the camera side magnet 55 may be disposed in parallel with the inner surface 30i of the abdominal wall 30, and the north and south poles of the fixing magnet 23 may be disposed in parallel with the outer surface 30s of the abdominal wall 30.

Because of the configuration, by rotating the camera fixing device 20 in an axial direction around the signal cable 25, the camera 5 on the inner surface 30i can be rotated following the movement of the camera fixing device 20. Therefore, an observation direction of the camera 5 can be changed without directly moving the camera 5 inside the body cavity.

The camera 5 in the present embodiment can be fixed by holding the body cavity wall (abdominal wall 30) by disposing the camera fixing device 20 on a patient without dissection of the body wall or without providing the through hole in the body wall. Therefore, the operator may dispose a plurality of cameras 5 inside the body cavity and perform a surgical operation by switching camera images. The operator may also change the position of the camera 5 by using the grasping forceps 93 or the like during a surgical operation as needed.

A camera 5A enabling to change the position of the camera 5 fixed to the inner surface of the body cavity during a surgical operation will be described with reference to FIGS. 14 to 19.

Figure 14:
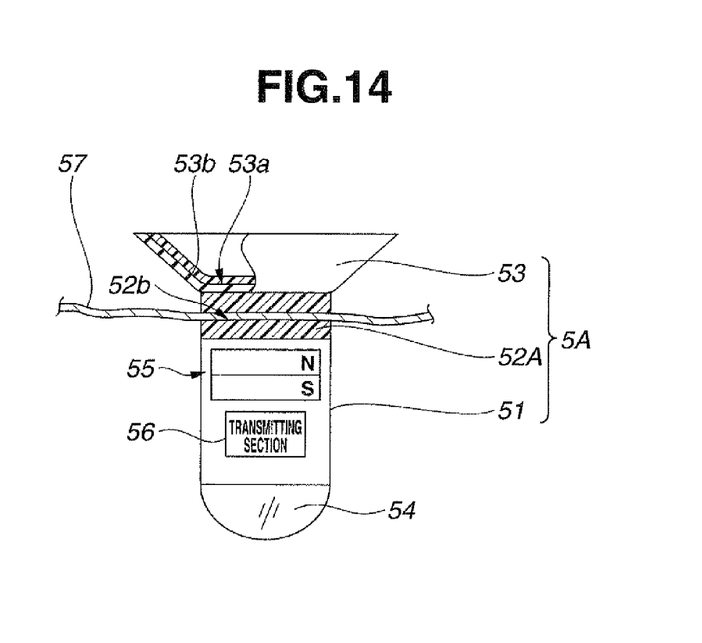
FIG. 14 is a view for explaining a configuration of a camera.
Figure 15:
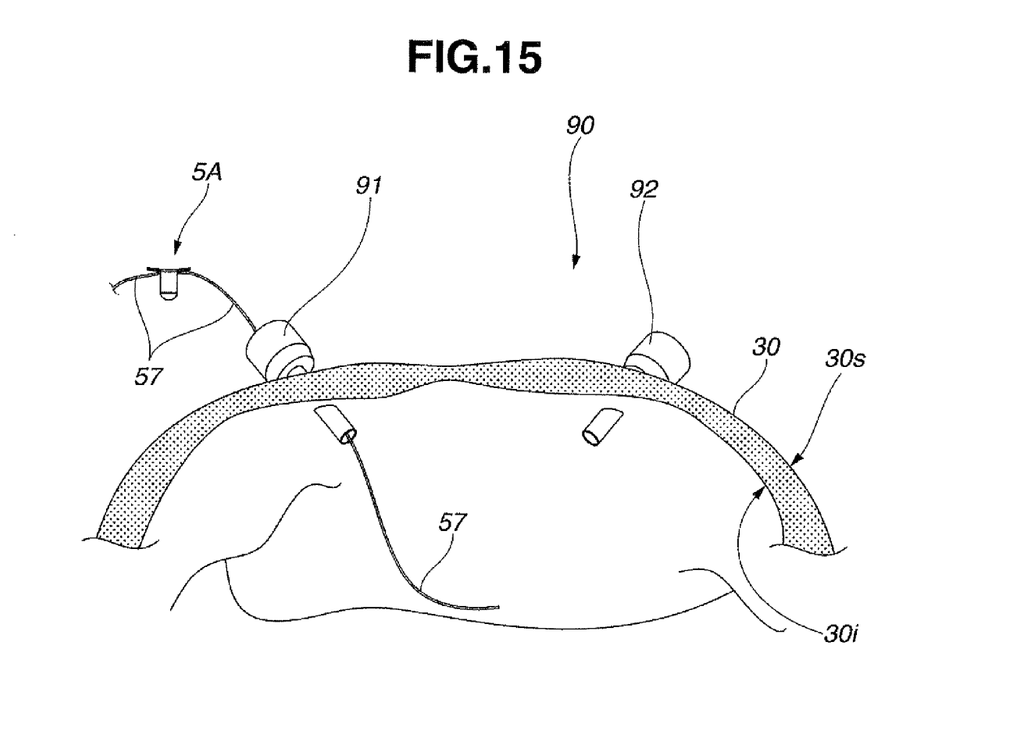
FIG. 15 is a view for explaining a state in which a camera moving wire of a camera is introduced from one trocar into an abdominal cavity.
Figure 16:
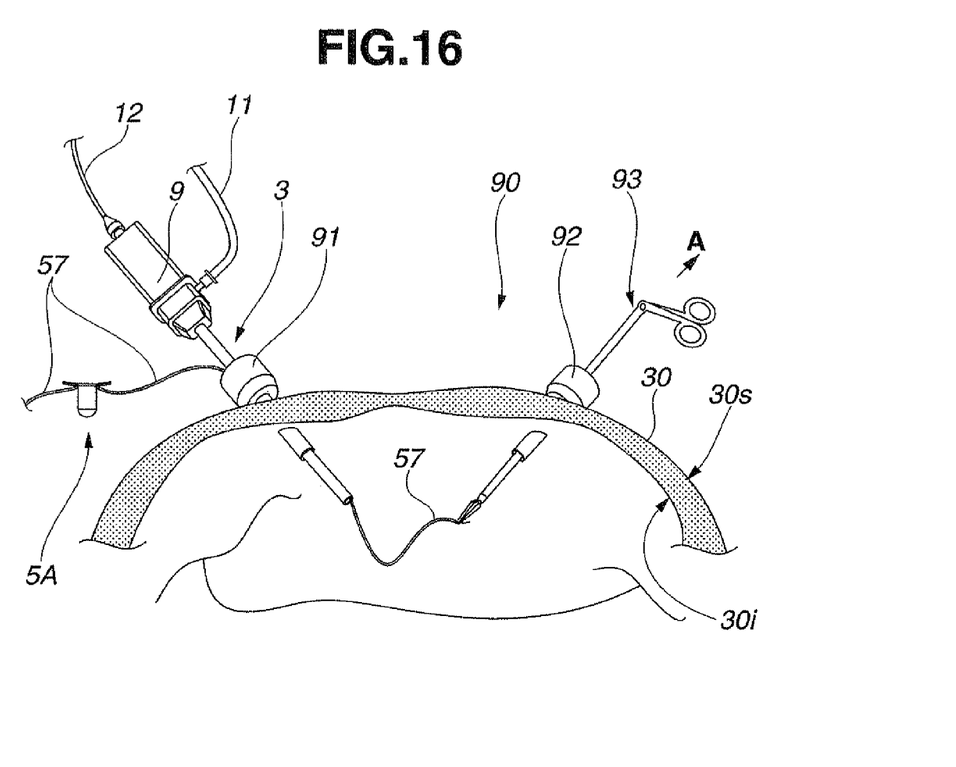
FIG. 16 is a view for explaining a state in which a camera moving wire is grasped by a grasping forceps and is drawn into the other trocar.
Figure 17:
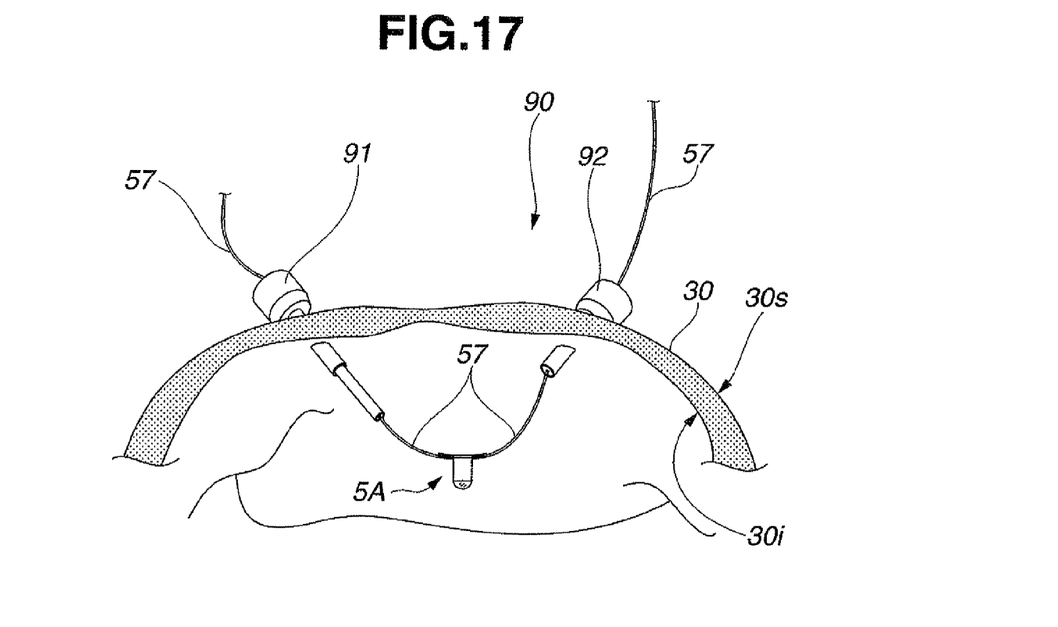
FIG. 17 is a view for explaining a state in which a camera is introduced into an abdominal cavity via a trocar by operating a camera moving wire.
Figure 18:
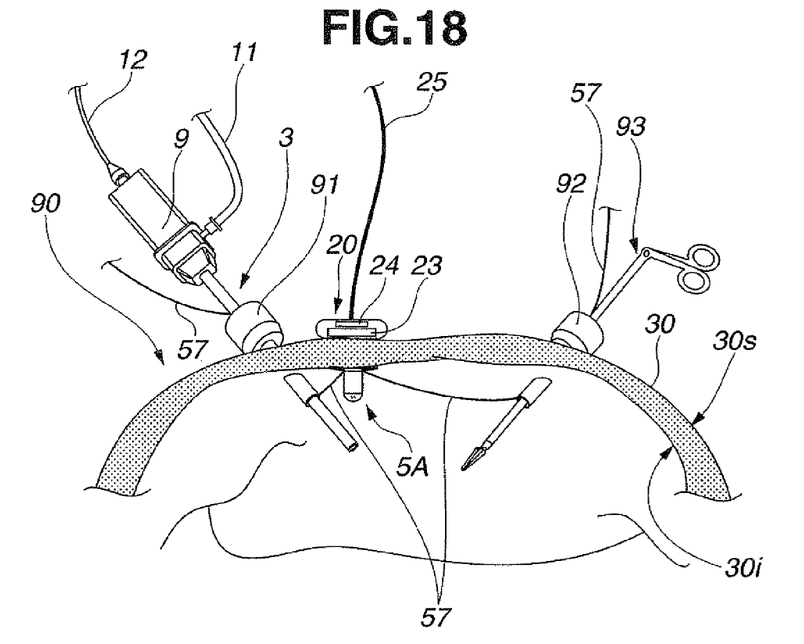
FIG. 18 is a view for explaining a state in which a camera is disposed on an inner surface of an abdominal wall.
Figure 19:
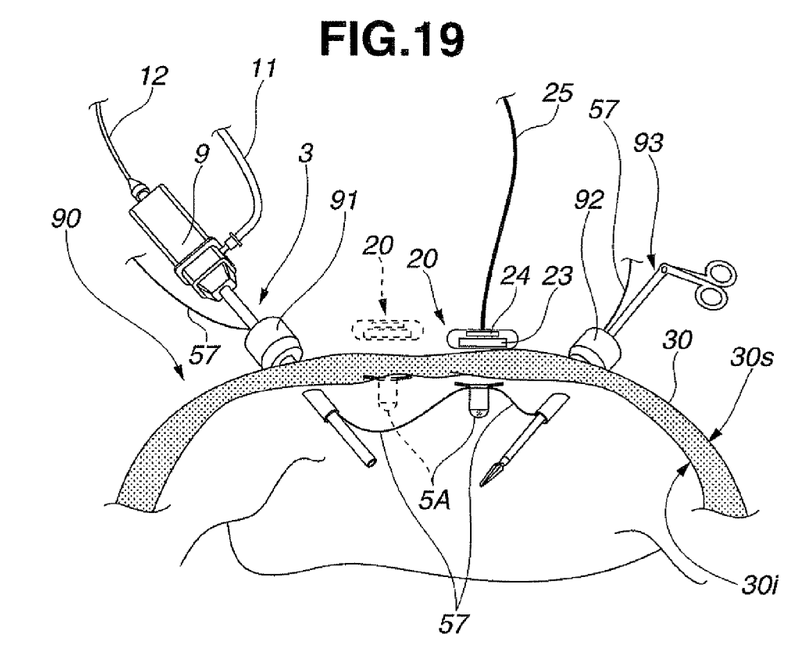
FIG. 19 is a view for explaining a state in which a camera position is changed by operating a camera moving wire.

FIG. 14 is a view for explaining a configuration of a camera; FIG. 15 is a view for explaining a state in which a camera moving wire provided to a camera is introduced from one trocar into an abdominal cavity; FIG. 16 is a view for explaining a state in which a camera moving wire is grasped by a grasping forceps and is drawn into the other trocar; FIG. 17 is a view for explaining a state in which a camera is introduced into an abdominal cavity via a trocar by operating a camera moving wire; FIG. 18 is a view for explaining a state in which a camera is disposed on an inner surface of an abdominal wall; and FIG. 19 is a view for explaining a state in which a camera position is changed by operating a camera moving wire.

The camera 5A shown in FIG. 14 is a camera with wire, and the camera 5A with wire includes a camera body 51, a base portion 52A, and an elastic portion 53. For example, a camera moving wire (abbreviated to wire below) 57 as a camera moving section which is camera moving means is fixedly provided to the base portion 52A.

In a present embodiment, the base portion 52A has a through hole 52b in a direction perpendicular to a longitudinal axis of the camera 5A with wire. The wire 57 is integrally fixed to the through hole 52b by an adhesive or a fixing member. The other configuration is the same as that of the embodiment described above, and the same members are assigned the same reference numerals to omit descriptions thereof. Note that the wire 57 may be configured to be able to move the camera 5A in one direction by a stopper member fixed to the wire 57 without integrally fixing the wire 57 to the base portion 52A.

An introduction procedure of the camera 5A with wire into a body cavity and its effect will be described with reference to FIGS. 15 to 19.

First, an operator introduces one end side of the wire 57 into an abdominal cavity by inserting the wire 57 of the camera 5A with wire into, for example, the trocar 91 which is penetrated into an abdomen of a patient 90 as shown in FIG. 15.

The operator inserts the rigid endoscope 3 into the trocar 91 into which the wire 57 is inserted as shown in FIG. 16. The operator observes an interior of the abdominal cavity by displaying the endoscope image on the screen of the first display device 7. The operator inserts the grasping forceps 93 into the trocar 92, and observes the endoscope image to draw the wire 57 into the trocar 92 by grasping one end side of the wire 57 and moving the grasping forceps 93 in a direction of an arrow A.

The operator removes the grasping forceps 93 from the trocar 92 and also, removes the rigid endoscope 3 from the trocar 91. The operator appropriately operates the wire 57 drawn from the trocar 92 and the wire 57 introduced into the trocar 91, to make the camera 5A with wire pass through the trocar 91 and introduce the camera 5A with wire into the abdominal cavity as shown in FIG. 17.

The operator brings the second CCU 6 into an ON state. The camera image is displayed on the screen of the second display device 8. The operator observes the camera image displayed on the second display device 8 and confirms whether the camera 5A with wire has been introduced into the abdominal cavity.

After the camera 5A with wire has been introduced into the abdominal cavity, the operator inserts the rigid endoscope 3 into the trocar 91 into which the wire 57 is inserted. The operator displays the endoscope image on the screen of the first display device 7 to observe the interior of the abdominal cavity. The operator also inserts the grasping forceps 93 into the trocar 92 into which the wire 57 is inserted.

The operator operates the wire 57 placed outside the body, and the grasping forceps 93 as needed, and fixes the camera 5A with wire to the inner surface 30i of the abdominal wall 30 as shown in FIG. 18 by positioning the camera fixing device 20 on a desired position of the outer surface 30s of the abdominal wall 30. Then, the operator performs a surgical operation with the camera 5A being fixed to the inner surface 30i.

The operator may change the position of the camera 5A with wire by operating the wire 57 and the grasping forceps 93 as needed as shown in FIG. 19 to perform a surgical operation.

After the surgical operation, the operator removes the grasping forceps 93 from the trocar 92, and then, removes the camera 5A with wire via the trocar 92 from the abdominal cavity by drawing the wire 57 to the operator side.

As described above, since the camera with wire is configured by providing the camera moving wire to the camera, the position of the camera with wire on the inner surface of the body cavity may be changed as needed by appropriately operating the camera moving wire or the grasping forceps during a surgical operation.

Note that the present invention is not limited to the embodiments as described above, and various modifications may be made without departing from the scope of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
    an endoscope configured to be inserted into a body through a first trocar;
    a camera disposed on a body cavity inner surface for picking up an image inside the body cavity, the camera comprising:
        a camera body incorporating a first magnet having a north pole and a south pole, one of which is disposed on a body wall surface side, an illuminating section and an image pickup section having a wide-angle lens disposed on a front surface of the illuminating section and the image pickup section, and
        an elastic contact surface portion provided on a body wall surface side of the camera body having a contact surface that deforms along an irregular body surface;
    a camera fixing device including a device body to be disposed on a skin outside the body cavity, the device body having inside thereof a second magnet having a north pole and a south pole, wherein one of the north and the south poles of the camera attracts the other of the north and the south poles of the second magnet disposed on a body wall surface side and wherein an attractive force between the first and second magnets causes the camera in the body cavity to be fixed on the body cavity inner surface with the abdominal wall being held between the fixing device and the camera and causes the camera to be directed toward an operation range of an operation instrument inserted through a second trocar;
    an adhesive configuring an adhesive layer provided on an entire contact surface of the elastic contact surface portion; and
    a control section for controlling the image pickup section.

2. The endoscope system according to claim 1, wherein the camera is disposed on the body cavity inner surface by a removing forceps inserted into the body through the second trocar.

* * * * *